(12) United States Patent
Najibi

(10) Patent No.: US 9,192,741 B1
(45) Date of Patent: Nov. 24, 2015

(54) CATHETER AND WIRE HOLDING DEVICE

(71) Applicant: Sasan Najibi, Encino, CA (US)

(72) Inventor: Sasan Najibi, Encino, CA (US)

( * ) Notice: Subject to any disclaimer, the term of this patent is extended or adjusted under 35 U.S.C. 154(b) by 33 days.

(21) Appl. No.: 14/298,566

(22) Filed: Jun. 6, 2014

(51) Int. Cl.
| | |
|---|---|
| *B65D 83/10* | (2006.01) |
| *A61M 25/00* | (2006.01) |
| *B65D 81/22* | (2006.01) |
| *B65D 33/00* | (2006.01) |
| *A61M 5/00* | (2006.01) |

(52) U.S. Cl.
CPC ............ *A61M 25/002* (2013.01); *B65D 33/008* (2013.01); *B65D 81/22* (2013.01); *A61M 5/007* (2013.01)

(58) Field of Classification Search
CPC ........... A61M 25/002; A61M 25/0113; A61B 19/0271; B65D 1/22; B65D 33/008
USPC .......... 206/207, 210, 570, 571, 572, 438, 5.1, 206/363–365; 604/174, 179; 128/202.19
See application file for complete search history.

(56) References Cited

U.S. PATENT DOCUMENTS

| | | | |
|---|---|---|---|
| 4,282,972 A | 8/1981 | Chiulli | |
| 4,519,793 A | 5/1985 | Galindo | |
| D290,403 S | 6/1987 | Sink | |
| 4,932,413 A | 6/1990 | Shockey | |
| 4,983,169 A | 1/1991 | Furukawa | |
| 4,988,356 A | 1/1991 | Crittenden | |
| 5,031,775 A | 7/1991 | Kane | |
| 5,125,416 A | 6/1992 | Phillips | |
| 5,165,540 A | 11/1992 | Forney | |
| D334,973 S | 4/1993 | Valentine | |
| 5,232,453 A | 8/1993 | Plass | |
| 5,611,428 A | 3/1997 | Banerian | |
| 5,769,222 A | 6/1998 | Banerian | |
| 5,810,781 A | 9/1998 | Bierman | |
| 5,827,202 A | 10/1998 | Miraki | |
| 5,827,230 A | 10/1998 | Bierman | |
| 5,843,002 A | 12/1998 | Pecor | |
| 6,015,119 A | 1/2000 | Starchevich | |
| 6,375,006 B1 | 4/2002 | Samuels | |
| 6,547,072 B2 | 4/2003 | Whiting | |
| 6,719,135 B2 | 4/2004 | Armijo | |
| 7,014,627 B2 | 3/2006 | Bierman | |
| 7,191,900 B2 | 3/2007 | Opie | |
| 7,993,389 B2 | 8/2011 | Globerman | |
| 8,016,793 B2 | 9/2011 | Wright | |
| D674,484 S | 1/2013 | Murphy | |
| D680,645 S | 4/2013 | Murphy | |
| D685,468 S | 7/2013 | Murphy | |
| 8,636,698 B2 | 1/2014 | Bierman | |
| 2002/0007159 A1 | 1/2002 | Mosel | |
| 2004/0255991 A1 | 12/2004 | Truwit | |
| 2005/0020940 A1 | 1/2005 | Opie | |
| 2006/0293631 A1 | 12/2006 | Bolt | |
| 2008/0108947 A1 | 5/2008 | Crawford | |
| 2008/0319387 A1 | 12/2008 | Amisar | |
| 2009/0043260 A1 | 2/2009 | Bierman | |
| 2009/0216197 A1 | 8/2009 | Russo | |
| 2011/0202038 A1 | 8/2011 | Gill | |
| 2012/0078232 A1 | 3/2012 | Schulting | |
| 2012/0172846 A1 | 7/2012 | Nakamoto | |
| 2012/0179033 A1 | 7/2012 | Merhi | |
| 2013/0304030 A1 | 11/2013 | Gray | |
| 2014/0005540 A1 | 1/2014 | Merhi | |
| 2014/0039398 A1 | 2/2014 | Rottenberg | |

*Primary Examiner* — Jacob K Ackun
*Assistant Examiner* — Rafael Ortiz
(74) *Attorney, Agent, or Firm* — Michael N. Cohen; Cohen IP Law Group, P.C.

(57) ABSTRACT

A catheter and guide wire holding device for storing a catheter and guide wire for angiographic procedures comprises at least one container filled with a saline solution, a plurality of pockets including a slit on the an upper panel of the plurality of pockets and a tab. The tab is utilized for holding together the plurality of pockets. The plurality of pockets is adapted to retain and receive the catheter and the guide wire without entanglement during angiographic procedures for later use.

17 Claims, 5 Drawing Sheets

CATHETER AND WIRE HOLDING DEVICE

CROSS-REFERENCE TO RELATED APPLICATIONS

Not Applicable.

STATEMENT REGARDING FEDERALLY SPONSORED RESEARCH AND DEVELOPMENT

Not Applicable.

FIELD OF THE DISCLOSURE

This embodiment relates to catheter holders, and more particularly to a catheter and guide wire holding device having a plurality of compartments adapted to retain and receive angiographic catheter and guide wires frequently used and reused during angiographic procedures.

DISCUSSION OF RELATED ART

Catheter and guide wires have been used in variety of medical applications, mostly for angiographic procedures and urinary bladder drainage techniques. Generally, catheter and guide wires are pre-packed in a receptacle by the manufacturer and easily disposable. During angiographic procedures, it is necessary that the catheter and guide wires be maintained in a sterile environment for later use with easy access. Attempts have been made to compensate for this by providing various kinds of catheter and guide wire holders that receive and retain catheter and guide wires for later use in a sterile condition for repeat use during the same procedure. The main function of these catheter and guide wire holders is to maintain easy access and provide space to hold more than one catheter and guide wire at a time and to be able to easily and readily access any particular catheter and guide wire for use.

Some angiographic catheter packages consist of a sterilized envelope pouch, an elongated tray, and a catheter tip restraint which retains the catheter tip therein in the desired shape. The tip restraint securely holds the catheter tip in the desired shape during sterilization and storage of the catheter and yet readily releases the catheter tip from the tip restraint when the user removes the catheter from the sterile package. However, such pans only hold one catheter at a time which causes difficulty for an operator during angiographic procedures that require multiple catheter and guide wires.

Certain containers are used during angiographic procedures for storing, cleansing, and moistening catheter and guide wires. These containers have a base and at least one upwardly and inwardly extending side wall. These containers may also have a plurality of standoff members to keep the coiled guide wire from touching the base and side walls of the container. A bathing solution may also be disposed within these containers to moisten and cleanse the coiled guide wire. The downside to these systems is that the catheter and guide wires can tangle up with each other and a specific catheter and guide wire, when needed, is not readily accessible to the operator for later use. Moreover, such systems are not compartmentalized and the catheters are not separated using any dividers. Thus, the catheters and guide wires tend to become entangled with each other, making it difficult and time consuming to separate the catheters.

Certain existing catheter pans for holding angiographic catheters and catheter and guide wires include a rectangular planar bottom portion, four walls upstanding from the ends thereof to form a basin adapted to retain liquid, a divider structure upstanding from the bottom portion and dividing the basin into a plurality of compartments, and an opposed pair of the walls inclined inwardly.

In light of the foregoing, there is a need for a simple, reusable, improved catheter and guide wire holding device with a container capable of holding a plurality of catheter and guide wires that are frequently used and reused during angiographic procedures in a sterile environment. Such a device would include dividers to separate the container into a plurality of compartments to provide easy access to any of the multiple catheter and guide wires for the operator without becoming intertwined with other stored catheters and guide wires. Further, such a device would include a container that is filled with a solution to keep the catheter and guide wires sterile and moist for later use. Furthermore, such a device would include multiple small holes in each of the compartments to allow free circulation of solution to prevent blood from sticking to the catheter and guide wires before use and reuse. Finally, such a device would include a holder with an aperture for holding catheter and guide wires. The aperture allows the operator to easily access and to remove the catheters and the guide wires from the holder. In addition, such a needed device would reliable and easy to handle. The present embodiment accomplishes these objectives.

SUMMARY OF THE DISCLOSURE

The present embodiment is a catheter and guide wire holding device for storing a catheter and guide wire for angiographic procedures comprises at least one container filled with a saline solution, a plurality of pockets includes a slit on upper panel and a tab. The tab is utilized for easy separation of the plurality of pockets. The plurality of pockets is adapted to retain and receive the catheter and guide wire without entanglement during angiographic procedures for later use.

The plurality of pockets of the catheter holding device further disposed with a plurality of holes thereof to allow the saline solution to pass through the plurality of pockets thereby maintaining a moist environment around the stored catheter and guide wires to diminish the blood particles attaching to the devices. The plurality of pockets can hold catheter and guide wires for angiographic procedures. The pluralities of pockets are held together utilizing a tab.

Other features and advantages of the present invention will become apparent from the following more detailed description, taken in conjunction with the accompanying drawings, which illustrate, by way of example, the principles of the invention.

DETAILED DESCRIPTION OF THE PREFERRED EMBODIMENT

The following describes example embodiments in which the present invention may be practiced. This invention, however, may be embodied in many different ways, and the description provided herein should not be construed as limiting in any way. Among other things, the following invention may be embodied as methods or devices. As such, the present invention may take the form of an entirely hardware embodiment, an entirely software embodiment, or an embodiment combining software and hardware aspects. The following detailed descriptions should not be taken in a limiting sense.

In this document, the terms "a" or "an" are used, as is common in patent documents, to include one or more than one. In this document, the term "or" is used to refer to a nonexclusive "or," such that "A or B" includes "A but not B," "B but not A," and "A and B," unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

Figure 1:
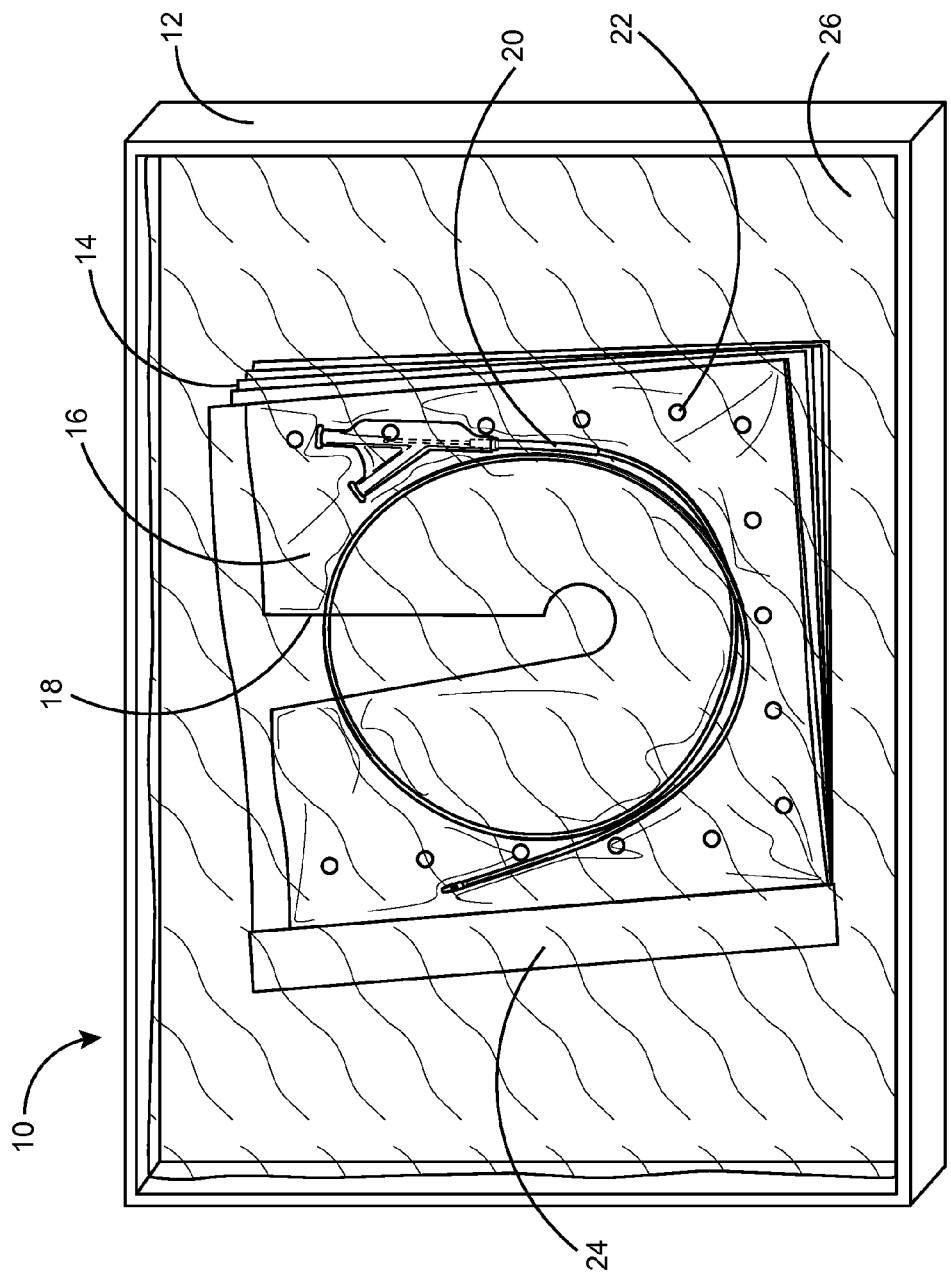
FIG. 1 is a front perspective view of a catheter and guide wire holding device in accordance with a preferred embodiment of the present invention.

Referring to FIG. 1, a catheter and guide wire holding device 10 in accordance with a preferred embodiment is illustrated. The catheter and guide wire holding device 10 comprises a container 12, a plurality of pockets 14, a holding a catheter and guide wire 20 having an upper panel 16 consisting of a slit 18 to grab the catheter and guide wire 20. The plurality of pockets 14 is disposed with a plurality of air holes 22 for the saline solution 26 to enter thereby maintaining a sterile atmosphere. The plurality of pockets 14 are attached together utilizing a tab 24. The plurality of pockets 14 is placed in saline solution 26 to maintain a sterile atmosphere.

Figure 2:
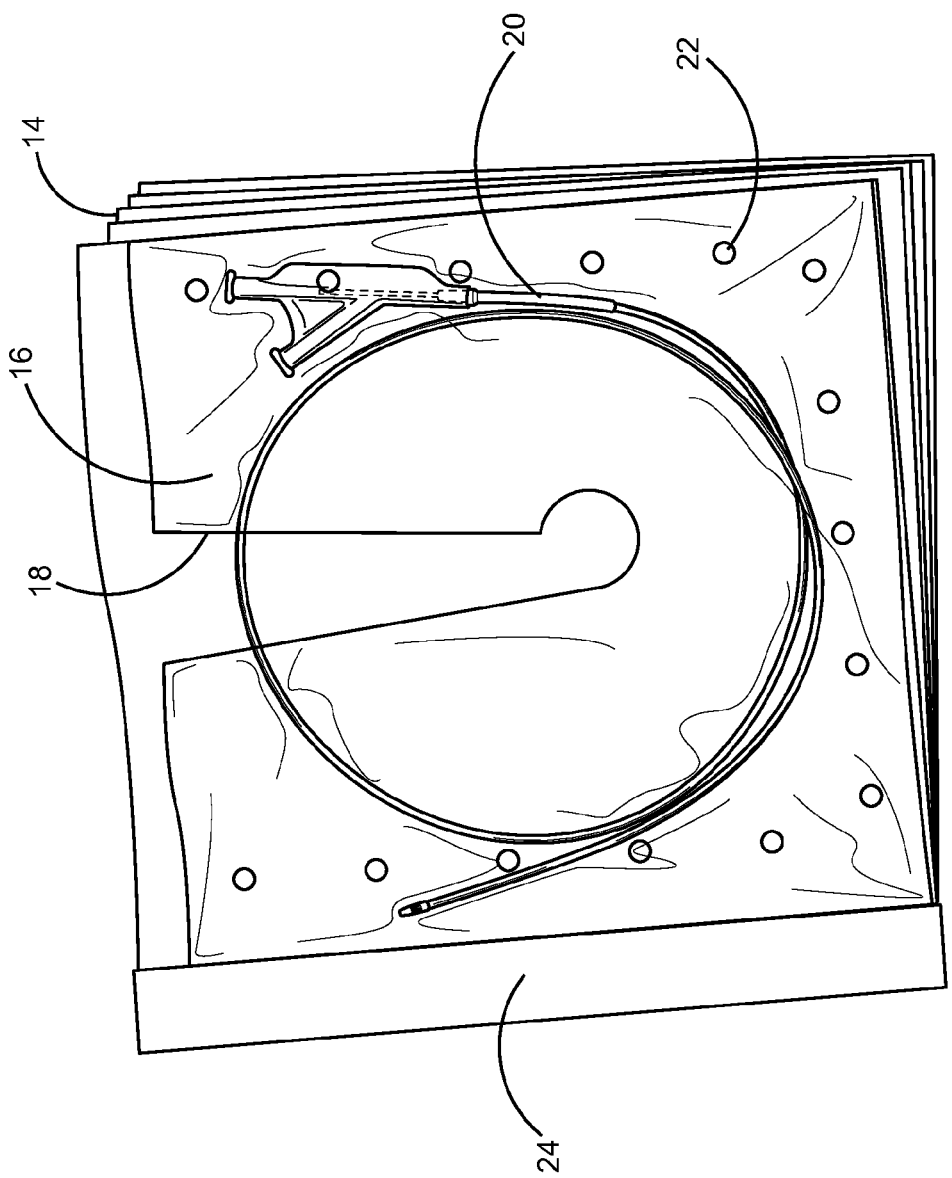
FIG. 2 is a front perspective view of a plurality of pockets associated with the catheter and guide wire holding device.

FIG. 2 illustrates the front perspective view of a plurality of pockets 14 associated with the catheter and guide wire holding device 10. The plurality of pockets 14 can hold the catheter and guide wires 20 for angiographic procedures. The plurality of pockets 14 can hold a numerous number of the catheter and guide wires 20 without entanglement. The plurality of pockets 14 is held together for utilizing a tab 24. The plurality of pockets 14 is disposed with the air holes 22 for the saline solution 26 to enter thereby maintaining a sterile atmosphere.

Figure 3:
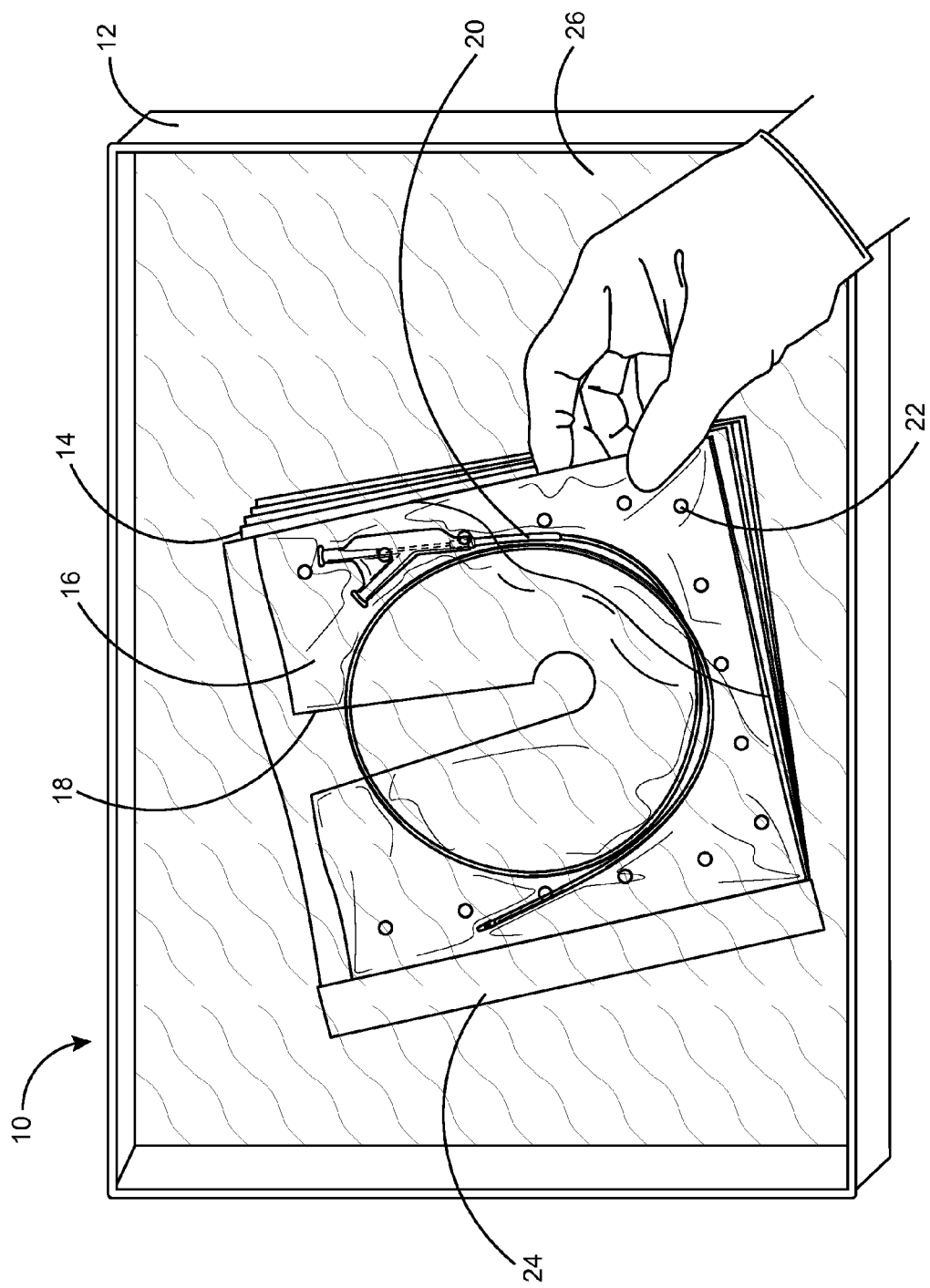
FIG. 3 illustrates a catheter and guide wire holding device in use.

FIG. 3 illustrates the catheter and guide wire holding device 10 in use. The plurality of pockets 14 can hold the catheter and guide wires 20 for angiographic procedures. The user may grab the catheter and guide wire 20 from the plurality of pockets 14 without entanglement. The plurality of pockets 14 is disposed with the holes 22 for the saline solution 26 to enter thereby maintaining a sterile atmosphere.

Figure 4:
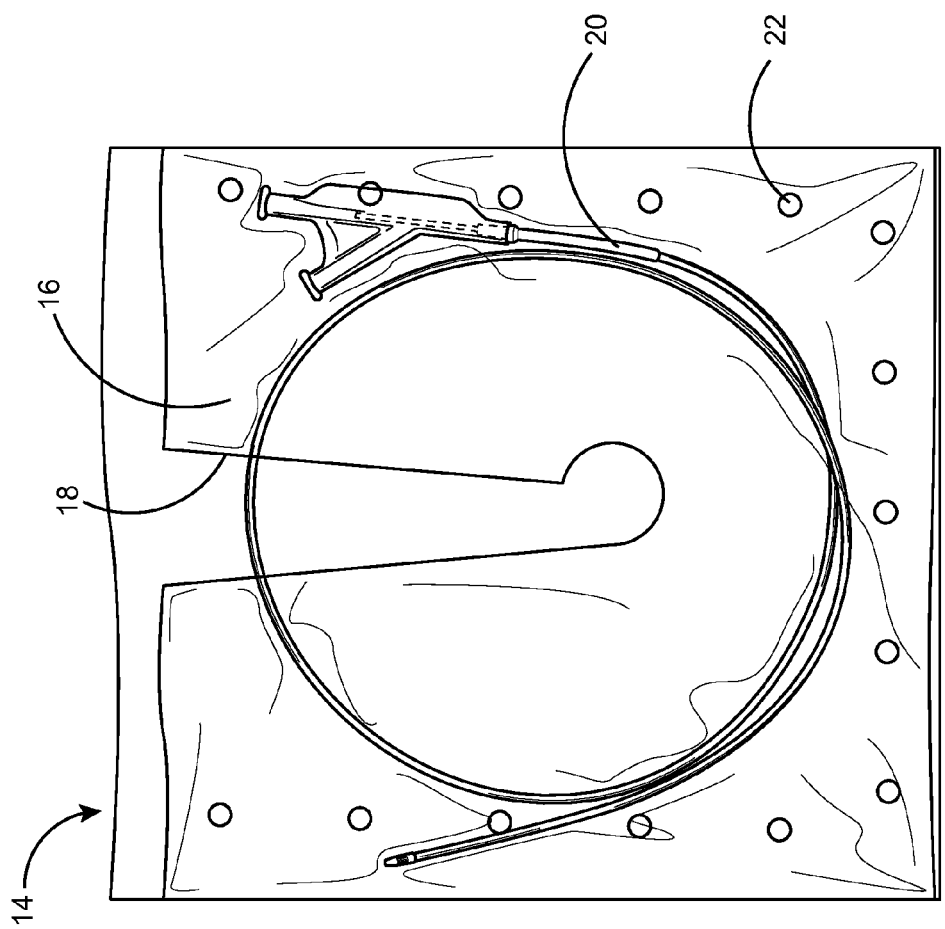
FIG. 4 is a front view of at least one pocket associated with the catheter and guide wire holding device.

FIG. 4 illustrates at least one pocket 14 in the catheter and guide wire holding device 10. The plurality of pockets 14 of the catheter and guide wire holding device 10 further disposed with the plurality of air holes 22 on the upper panel 16 thereof to allow the saline solution 26 to pass through the plurality of pockets 14. The plurality of pockets 14 is made of soft plastic. The plurality of pockets 14 can hold the catheter and guide wires 20 for angiographic procedures. The plurality of pockets 14 is capable of preventing the entanglement of the catheter and guide wire 20 with other stored catheter guide wires 20.

Figure 5:
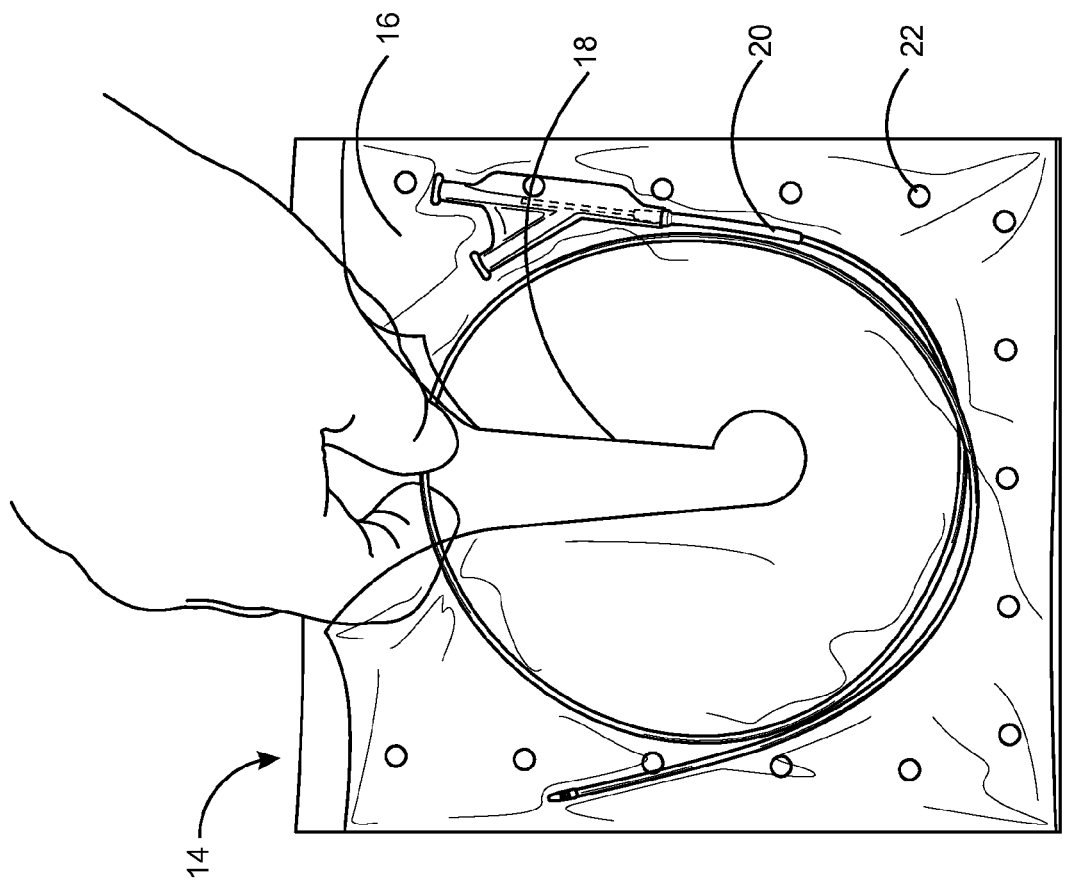
FIG. 5 is a front view of at least one pocket associated with the catheter and guide wire holding device in use.

FIG. 5 shows one of the pluralities of pockets 14 in the catheter and guide wire holding device 10. The plurality of pockets 14 of the catheter and guide wire holding device 10 is further disposed with the plurality of holes 22 on the upper panel 16 thereof to allow the saline solution 26 to pass through the plurality of pockets 14. The plurality of pockets 14 is made of soft plastic. The plurality of pockets 14 can hold the catheters and guide wires 20 for angiographic procedures. The plurality of pockets 14 is capable of preventing the entanglement of the catheter and guide wire 20 with other stored catheter and guide wires 20.

While a particular form of the invention has been illustrated and described, it will be apparent that various modifications can be made without departing from the spirit and scope of the invention. Accordingly, it is not intended that the invention be limited, except as by the appended claims.

What is claimed is:

1. A catheter and guide wire holding device comprising:
   at least one container filled with a saline solution;
   a plurality of pockets, each pocket includes a slit on an upper panel; thereof, the plurality of pockets being adapted to hold a catheter and guide wire; and
   a tab utilized for holding together the plurality of pockets;
   whereby the plurality of pockets is adapted to retain and receive the catheter and guide wire without entanglement during angiographic procedures for later use.

2. The catheter and guide wire holding device of claim 1 wherein the plurality of pockets is further disposed with a plurality of holes on the upper and lower panel thereof to allow the saline solution to pass through the plurality of pockets.

3. The catheter and guide wire holding device of claim 1 wherein the saline solution submerges the catheter and the guide wire when not in use.

4. The catheter and guide wire holding device of claim 1 wherein the saline solution filled in the at least one container provides a sterile environment.

5. The catheter and guide wire holding device of claim 1 wherein each of the plurality of pockets is capable of preventing the entanglement of the catheter and the guide wire with other stored catheters guide wires.

6. The catheter and guide wire holding device of claim 1 wherein the slit allows an operator to easily access and remove the catheter and the guide wire from the plurality of pockets during the angiographic procedures.

7. The catheter and guide wire holding device of claim 1 wherein the plurality of pockets is made of soft plastic.

8. A catheter and guide wire holding device for storing a catheter and a guide wire comprising:
   at least one container filled with a saline solution;
   a plurality of pockets, each pocket includes an opening on an upper and lower panels thereof, the plurality of pockets being adapted to hold a catheter guide wire; and
   a tab utilized for holding together the plurality of pockets;
   whereby the plurality of pockets is adapted to retain and receive the catheter and guide wire without entanglement during angiographic procedures for later use.

9. The catheter and guide wire holding device of claim 8 wherein the saline solution submerges the catheter and the guide wire when not in use.

10. The catheter and guide wire holding device of claim 8 wherein the saline solution filled in the at least one container provides a sterile environment.

11. The catheter and guide wire holding device of claim 8 wherein the slit allows an operator to easily access and remove the catheter and the guide wire from the plurality of pockets during the angiographic procedures.

12. The catheter and guide wire holding device of claim 8 wherein the plurality of pockets is capable of preventing the entanglement of the catheter guide wire with other stored catheters guide wires.

13. The catheter and guide wire holding device of claim 8 wherein the plurality of pockets is made of soft plastic.

14. A catheter and guide wire holding device for storing a catheter guide wire for angiographic procedures comprising:
- at least one container filled with a saline solution;
- a plurality of pockets, each pocket includes an opening on an upper and lower panel thereof, the plurality of pockets being adapted to hold a catheter and guide wire to hold the catheters; and
- a tab utilized for holding together the plurality of pockets;
- whereby the plurality of pockets is adapted to retain and receive the catheter and guide wire without entanglement during angiographic procedures for later use.

15. The catheter and guide wire holding device of claim 14 wherein the saline solution filled in the container provides a sterile atmosphere.

16. The catheter and guide wire holding device of claim 14 wherein the slit allows an operator to grab the catheter guide wire during the angiographic procedures.

17. The catheter and guide wire holding device of claim 14 wherein the plurality of pockets is capable of preventing the entanglement of the catheter guide wire with other stored catheters guide wires.

\* \* \* \* \*